(12) United States Patent
Bernardo et al.

(10) Patent No.: US 7,733,466 B2
(45) Date of Patent: Jun. 8, 2010

(54) MEASUREMENT OF CONSTITUTIVE PROPERTIES OF A POWDER SUBJECT TO COMPRESSIVE AXIAL AND RADIAL LOADING, USING OPTICAL SENSING

(75) Inventors: Alexander Beltran Bernardo, San Antonio, TX (US); Gary Lane Burkhardt, Adkins, TX (US); Arthur Edwin Nicholls, Helotes, TX (US); Walter Mac Gray, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 336 days.

(21) Appl. No.: 11/872,525

(22) Filed: Oct. 15, 2007

(65) Prior Publication Data
US 2009/0128801 A1 May 21, 2009

(51) Int. Cl.
*G01N 3/08* (2006.01)
*G01B 11/16* (2006.01)

(52) U.S. Cl. .............................. 356/32; 73/760; 73/818
(58) Field of Classification Search ......... 356/625–640; 73/818, 760; 250/559.12, 559.19, 559.24, 250/559.29, 356
See application file for complete search history.

(56) References Cited

U.S. PATENT DOCUMENTS

| | | | | |
|---|---|---|---|---|
| 3,664,473 | A | 5/1972 | Hendershot, Jr. et al. | 192/21.5 |
| 3,693,420 | A * | 9/1972 | Wray et al. | 73/81 |
| 4,596,470 | A * | 6/1986 | Park | 374/14 |
| 4,703,316 | A * | 10/1987 | Sherbeck | 345/175 |
| 4,748,332 | A * | 5/1988 | Kuhne et al. | 250/559.24 |
| 4,852,451 | A | 8/1989 | Rogers | 86/33 |
| 5,113,591 | A * | 5/1992 | Connelly | 33/550 |
| 5,359,418 | A * | 10/1994 | Zaleski | 356/640 |
| 5,635,724 | A * | 6/1997 | Higgins | 250/559.19 |
| 5,864,239 | A | 1/1999 | Adams et al. | 324/636 |
| 6,922,254 | B2 * | 7/2005 | Blohm et al. | 356/638 |
| 7,161,687 | B2 * | 1/2007 | Pirinoli | 356/625 |
| 7,288,941 | B2 | 10/2007 | Redko et al. | 324/450 |
| 7,295,329 | B2 * | 11/2007 | Gruhlke et al. | 356/614 |
| 7,452,166 | B2 * | 11/2008 | von Keudell et al. | 406/98 |
| 7,469,596 | B1 * | 12/2008 | Bernardo et al. | 73/818 |

* cited by examiner

*Primary Examiner*—Sang Nguyen
(74) *Attorney, Agent, or Firm*—Baker Botts LLP

(57) ABSTRACT

A method and system for measuring radial strain on powder or other granular material while the powder is subject to compressive axial and radial loading. The powder is contained within a pliable sleeve. As pressure is applied to the powder, the sleeve changes diameter. An optical emitter emits a beam of light, which is intersected by the entire diameter of the sleeve. An optical sensor receives the intersected beam, and generates a response signal that indicates the diameter of the sleeve. This change in diameter can be related to a constitutive property such as strain.

14 Claims, 1 Drawing Sheet

MEASUREMENT OF CONSTITUTIVE PROPERTIES OF A POWDER SUBJECT TO COMPRESSIVE AXIAL AND RADIAL LOADING, USING OPTICAL SENSING

TECHNICAL FIELD OF THE INVENTION

This invention relates to measuring constitutive properties, such as radial strain, on a specimen of powder or other granular material while the specimen is subject to compressive axial and radial loading

BACKGROUND OF THE INVENTION

The relationship between stress and strain of powders or granular materials can be difficult to determine. Unlike a specimen of solid material, a specimen of powder cannot be easily placed under uniaxial stress and examined. For example, for testing steel, a small piece of steel can be used as a specimen, placed under uniaxial stress, whereupon the resulting strain can be measured.

Because of their inherent nature, powders and granular materials must first be loaded in all three directions (triaxially) in an initial hydrostatic (pressure all around) condition. This permits the load on one of the axes to be increased to obtain the strain response of the loaded axis.

One approach to loading a powder specimen triaxially is to provide a specimen having a right circular cylinder geometry. The specimen is subjected to constant confining pressure, using hydraulic pressure in the radial direction while varying the load in the long axis with mechanical means. This allows measurement of strain in the long axis, but measurement of strain in the radial direction becomes challenging, as strains in that direction can be upwards of 50%. A common strain gage is inadequate for this type of measurement.

For powders, properties such as the relationship between stress and strain or the Poisson's ratio, are referred to as "constitutive" properties. Once known, these properties can be used to predict the behavior of powders for diverse applications.

To determine constitutive properties, a small specimen of powder (or other granular material) can be evaluated, and its measured properties can then be used to predict the behavior of large amounts of the powder. The measurements can be used in simulations and other calculations. For example, if the properties of a sand specimen were to be measured, the penetration of a ballistic projectile into sandy terrain could then be simulated. If, in another example, measurements were made on an asteroid's response to a human-induced impact event, the results could be compared with simulations of the event using material characteristics of a catalog of powders and granular materials to verify the asteroid's composition.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION OF THE INVENTION

The following description is directed to a method and system for measuring radial strain of powders and granular materials subject to compressive axial loading while radial pressure is being applied with hydraulic fluid.

Figure 1:
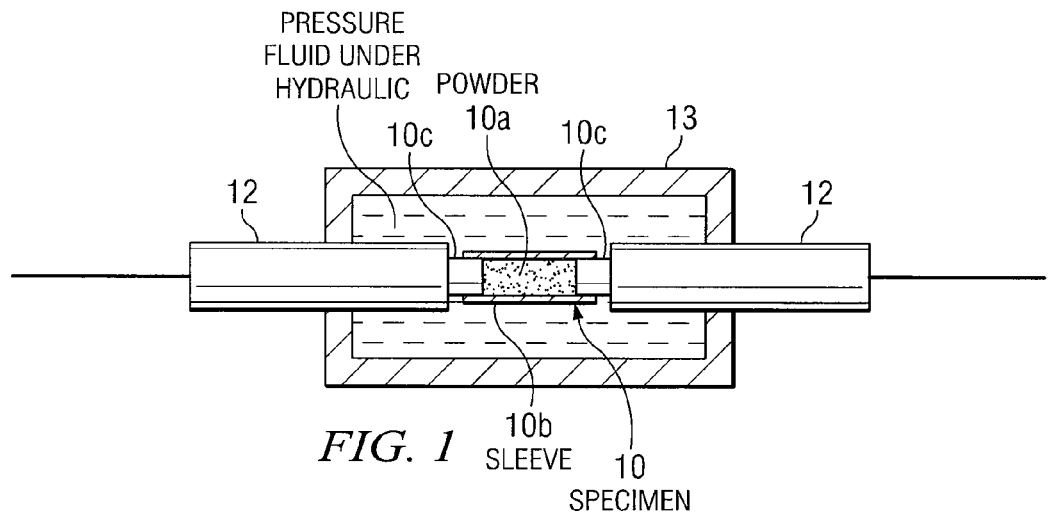
FIG. 1 illustrates a specimen of powder that is compressed by both axial loading and hydraulic confinement.

FIG. 1 illustrates a specimen 10 subject to both axial and radial compression. The specimen 10 is a sample of a powder of interest 10a, contained by a cylindrically shaped pliable sleeve 10b and two plug-type end caps 10c.

FIG. 1 further represents equipment for loading the specimen 10, shown representatively by two opposing loading bars 12 and a hydraulic chamber 13, which are part of larger loading equipment. Examples of suitable equipment for applying axial loading are an MTS servo-hydraulic machine, or a Split-Hopkinson Pressure Bar technique. The loading bars 12 are moveable into chamber 13, which is filled with a hydraulic fluid for the purpose of applying a constraining radial force on the specimen 10.

Sleeve 10b may be made from various materials, but requires rigidity at small stresses and flexibility at high stresses. An example of a suitable material for sleeve 10b is Teflon or some other elastomeric material. The material and thickness of sleeve 10b can be adjusted to provide the desired amount of axial and radial compression for the particular powder 10a under test.

End caps 10c are made from a material that can withstand the axial loads described below. Examples of suitable materials are steel and ceramic.

For purposes of this description, a "powder" is used in a general sense to apply to any type of powder or granular material that is processed by applying compressive loading. An example of a suitable specimen size is 0.25 inches diameter and 0.5 inches long. Other specimen geometries and sizes may be used.

In practice, one cap 10c is first inserted into one end of sleeve 10b, which is then filled with powder or other granular material of interest from the other end. The powder is compacted into the sleeve 10b, and the other cap 10c is inserted in the open end of the sleeve 10b. As a result, the powder is symmetrically sandwiched between the caps 10c.

The end caps 10c are each axially slideable into their respective end of sleeve 10b. In the example of FIG. 1, each end cap 10c extends beyond sleeve 10b so that it can be pressed into sleeve 10b thereby compressing the powder 10a.

The specimen 10 is positioned between the loading bars 12 in the chamber 13. The chamber 13 is then filled with the hydraulic fluid. The hydraulic fluid and the loading bars are simultaneously loaded to generate hydrostatic pressure on the specimen 10. That is, the axial load and the radial load impart equal pressure on the specimen 10 in all directions. The axial load from the loading bars 12 is translated to the powder 10a through the caps 10c. As stated above, the caps 10c are slideable within sleeve 10b so that the powder is compressed and exerts a radial response against the sleeve 10b. This causes sleeve 10b to increase in diameter.

Once hydrostatic pressure is achieved, the axial loading is increased and the axial and radial strain response can be measured. The axial load can be slow or fast (ranging from 10e-5 strain per second to 10e3 strain per second). Hydraulic fluid continues to impart confining pressure on specimen 10, while it is subject to the axial loading. The hydraulic loading is kept at a constant pressure while the axial load is increased.

In practice, the equipment is often operated so that the initial loading is uniform on the ends (from the axial loading)

and sides (from the radial loading) of the sleeve 10b. The measurement of strain in the axial direction is achieved using methods not discussed here.

Under the loading conditions of FIG. 1, the specimen 10a can be made to undergo large radial strains (up to 50%). Strain gages are not useful for measuring this type of strain.

Figure 2:
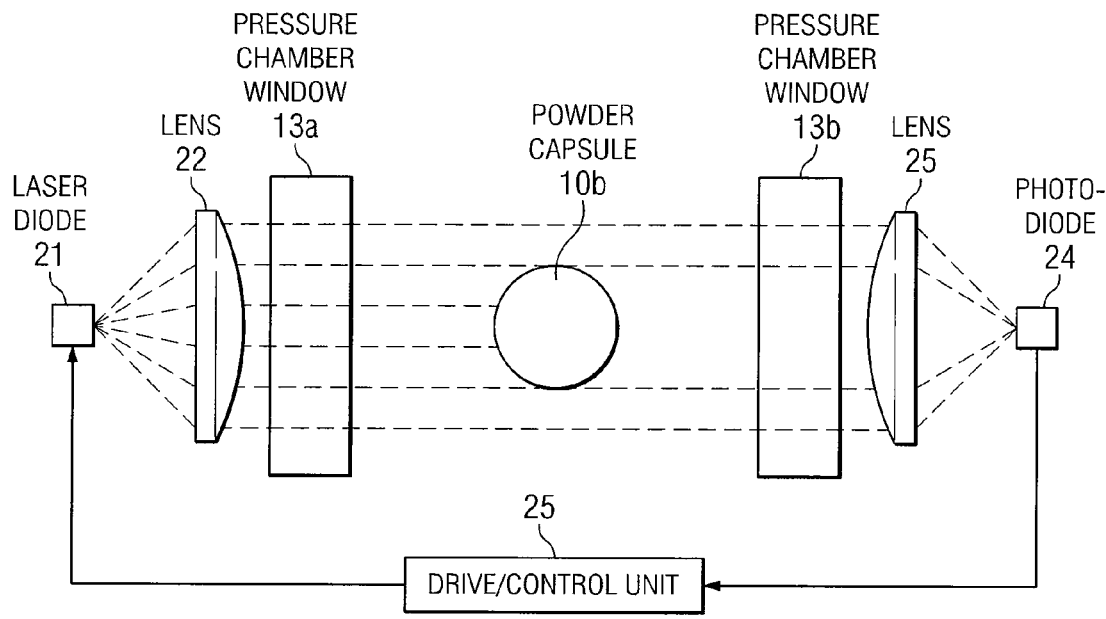
FIG. 2 illustrates a system and method for measuring radial strain of the specimen of FIG. 1.

FIG. 2 illustrates a system and method for optically measuring the radial strain imposed upon specimen 10. The specimen 10 is shown as an end view. The test equipment is not explicitly shown, other than by windows 13a and 13b in chamber 13.

The method is based on measuring the change in diameter of the specimen 10 by sensing the proportion of a light beam that is interrupted by the specimen 10. Optical sensing employs windows in the pressure chamber 13, sized and located to accommodate transmission of the light beam through the hydraulic fluid in chamber 13 and past specimen 10.

More specifically, an optical emitter 21 generates a light beam that is spread to the desired size area using a lens 22. An example of a suitable emitter 21 is a laser diode. Emitter 21 must provide a beam that is sufficient in intensity to penetrate windows 13a and 13b and the hydraulic fluid in chamber 13.

The beam from emitter 21 is sufficiently large in size so that the entire diameter of specimen 10 will intersect the beam, and so that the beam is larger in diameter than the specimen 10. An example of a suitable beam cross-section is one that is 50% larger than the diameter of the specimen 10.

The optical beam is then passed through window 13a in the chamber 13. As an option, the optical beam can be shaped to form a line beam, such as by a slit in of front of the emitter. The beam passes along an optical path through chamber 13, and out chamber 13 via a window 13b. After exiting chamber 13, the beam is focused onto an optical sensor 24 using an additional lens 25.

Windows 13a and 13b are sized and located to transmit the beam from emitter 21 into window 13a, through the hydraulic fluid past specimen 10, and out window 13b. Windows 13a and 13b are designed to withstand high pressure within chamber 13, which could be as much as 50,000 psi. An example of a suitable window material is 1 inch thick sapphire.

As shown in FIG. 2, the beam is partially interrupted by the specimen 10. As the specimen 10 changes diameter, more or less of the beam is interrupted. The voltage output of the sensor 24 is proportional to the amount of light striking it. Thus, the amount of light can be related to the diameter of specimen 10. A change in diameter of specimen 10 will result in a change in output voltage of the sensor 24.

An optical sensor 24 with sufficient rise time is used. An example of a suitable sensor 24 is a photodiode. An example of a suitable rise time is 1 ns.

Drive/control unit 25 provides appropriate electrical control and power signals to drive emitter 21. It also receives an electrical signal representing the amount of light detected by sensor 24.

Drive/control unit 25 may further have appropriate processing and memory for performing an analysis of the electrical response from sensor 24. Specifically, unit 25 may have memory for storing relationships between the signal received from sensor 24 and changes in diameter of the sleeve 10b. Unit 25 may be further programmed to relate the changes in diameter to one or more constitutive properties such as a strain value.

Drive/control unit 25 may also have timing and control circuitry for controlling the measurement rate. Unit 25 could be separate from, or integrated with, other control circuitry for controlling the test equipment (i.e., the compression applied by bars 12 and hydraulic fluid in chamber 13).

In sum, the system and method described herein permit radial strain measurements caused by increasing axial load to be made, while the specimen is in hydraulic fluid confinement, imparting radial pressure to the specimen. This method allows quantification of the fundamental response of powder and granular materials to such loading forces.

What is claimed is:

1. A method for measuring a constitutive property of a powder, comprising:

filling a cylindrically shaped pliable sleeve with a sample of the powder;

applying compressive force to the sample, such that the diameter of the sleeve changes;

imposing an optical beam across the sleeve, such that the cross section of the beam is larger than the diameter of the specimen and is intersected by the entire diameter of the sleeve;

using an optical sensor to detect the portion of the beam not intersected by the sleeve;

using a processor and memory to perform the following steps: receive an electrical response signal from the photodetector that represents a change in diameter of the sleeve;

relate the response signal to the diameter of the sleeve;

relate the change in diameter of the sleeve to a constitutive property of the powder; and store the results of the preceding step.

2. The method of claim 1, wherein the compressive force is an axial force on the sample from each end of the sleeve.

3. The method of claim 1, wherein the axial force is applied to a cap on each end of the sleeve.

4. The method of claim 1, wherein the compressive force is a radial force, achieved by placing the sleeve in a hydraulic chamber.

5. The method of claim 4, wherein the emitter and detector are located on opposing sides of the chamber, and wherein the chamber has a first window for allowing the beam from the emitter to enter the chamber and an opposing second window for allowing the beam intersected by the sleeve to exit the chamber.

6. The method of claim 5, wherein the beam is a line beam.

7. The method of claim 5, wherein the imposing step is performed using a laser diode.

8. The method of claim 1, wherein the sensor is a photodiode.

9. The method of claim 1, wherein the sleeve is made from an elastomeric material.

10. The method of claim 1, wherein the constitutive property is radial strain as a function of axial load.

11. A system for measuring a constitutive property of a sample of a powder contained in a cylindrically shaped pliable sleeve, comprising:

test equipment for applying compressive forces to the sample, such that the diameter of the sleeve changes size;

wherein the test equipment has a hydraulic chamber for applying compressive force to the sample when the sleeve is installed into the chamber;

an optical emitter outside the chamber for emitting an optical beam in the direction of the sleeve;

an optical sensor for detecting the beam after it is intersected by the sleeve;

wherein the chamber has a first window for allowing the beam from the emitter to enter the chamber and an opposing second window for allowing the beam intersected by the sleeve to exit the chamber; and a drive/control unit for applying an electrical drive signal to the emitter, and for receiving an electrical response signal from the sensor that represents changes in the amount of light received by the sensor.

12. The system of claim 11, wherein the drive/control unit has data processing and storage circuitry for relating the response signal to the diameter of the sleeve.

13. The system of claim 12, wherein the data processing and storage circuitry stores data that relates changes in diameter of the sleeve to a constitutive property of the powder.

14. The system of claim 13, wherein the constitutive property is radial strain.

* * * * *